(12) United States Patent
Ball et al.

(10) Patent No.: US 9,161,816 B2
(45) Date of Patent: Oct. 20, 2015

(54) FLUOROSCOPY C-ARM DRAPE CLIP, DRAPE CLIP ASSEMBLY AND METHOD OF CLIPPING A STERILE DRAPE TO A FLUOROSCOPY C-ARM

(75) Inventors: Bruce W. Ball, Flushing, MI (US); Clifford S. Parsons, Flushing, MI (US)

(73) Assignee: TIDI CFI Products, LLC, Fenton, MI (US)

( * ) Notice: Subject to any disclaimer, the term of this patent is extended or adjusted under 35 U.S.C. 154(b) by 548 days.

(21) Appl. No.: 13/561,939

(22) Filed: Jul. 30, 2012

(65) Prior Publication Data

US 2013/0025605 A1    Jan. 31, 2013

Related U.S. Application Data

(60) Provisional application No. 61/513,074, filed on Jul. 29, 2011.

(51) Int. Cl.
*A61B 19/08* (2006.01)
*A61B 6/00* (2006.01)
*A61B 17/28* (2006.01)

(52) U.S. Cl.
CPC ............ *A61B 19/081* (2013.01); *A61B 6/4423* (2013.01); *A61B 6/4441* (2013.01); *A61B 6/4405* (2013.01); *A61B 6/487* (2013.01); *A61B 2017/2808* (2013.01)

(58) Field of Classification Search
CPC ................. A61B 19/08; A61B 19/081; A61B 2017/2808; A61B 6/4441; A61B 6/4423; A61B 6/4405; F16B 2/00; F16B 2/20; F16B 2/22
See application file for complete search history.

(56) References Cited

U.S. PATENT DOCUMENTS

| 5,813,409 | A | * | 9/1998 | Leahy et al. | ................... 128/897 |
| 6,460,715 | B1 | * | 10/2002 | Yonemori et al. | ............ 215/396 |
| 7,833,150 | B2 | | 11/2010 | Yamamoto et al. | |
| 8,894,616 | B2 | | 11/2014 | Harrison et al. | |
| 2011/0154623 | A1 | * | 6/2011 | Schmidt et al. | .................. 24/457 |

FOREIGN PATENT DOCUMENTS

FR         2072241      9/1971
WO    WO 9717035  A1 *  5/1997

* cited by examiner

*Primary Examiner* — Victoria J Hicks
*Assistant Examiner* — Kari Petrik
(74) *Attorney, Agent, or Firm* — Boyle Fredrickson, S.C.

(57) ABSTRACT

A fluoroscopy C-arm drape clip for attaching a sterile drape to a C-arm of a fluoroscopy C-arm imaging unit and method of providing a sterile outer surface on a C-arm of a fluoroscopy C-arm imaging unit is provided. The drape clip includes a generally U-shaped band having a pair of legs and an arm. Each of the legs has a first end attached to the arm and a second end spaced from the arm. The legs extend away from the arm in non-parallel, laterally spaced relation with one another and have inner surfaces facing one another and an outer surfaces facing away from one another. Further, an elastic pad is attached to the inner surface of each of the legs adjacent the second ends.

18 Claims, 3 Drawing Sheets

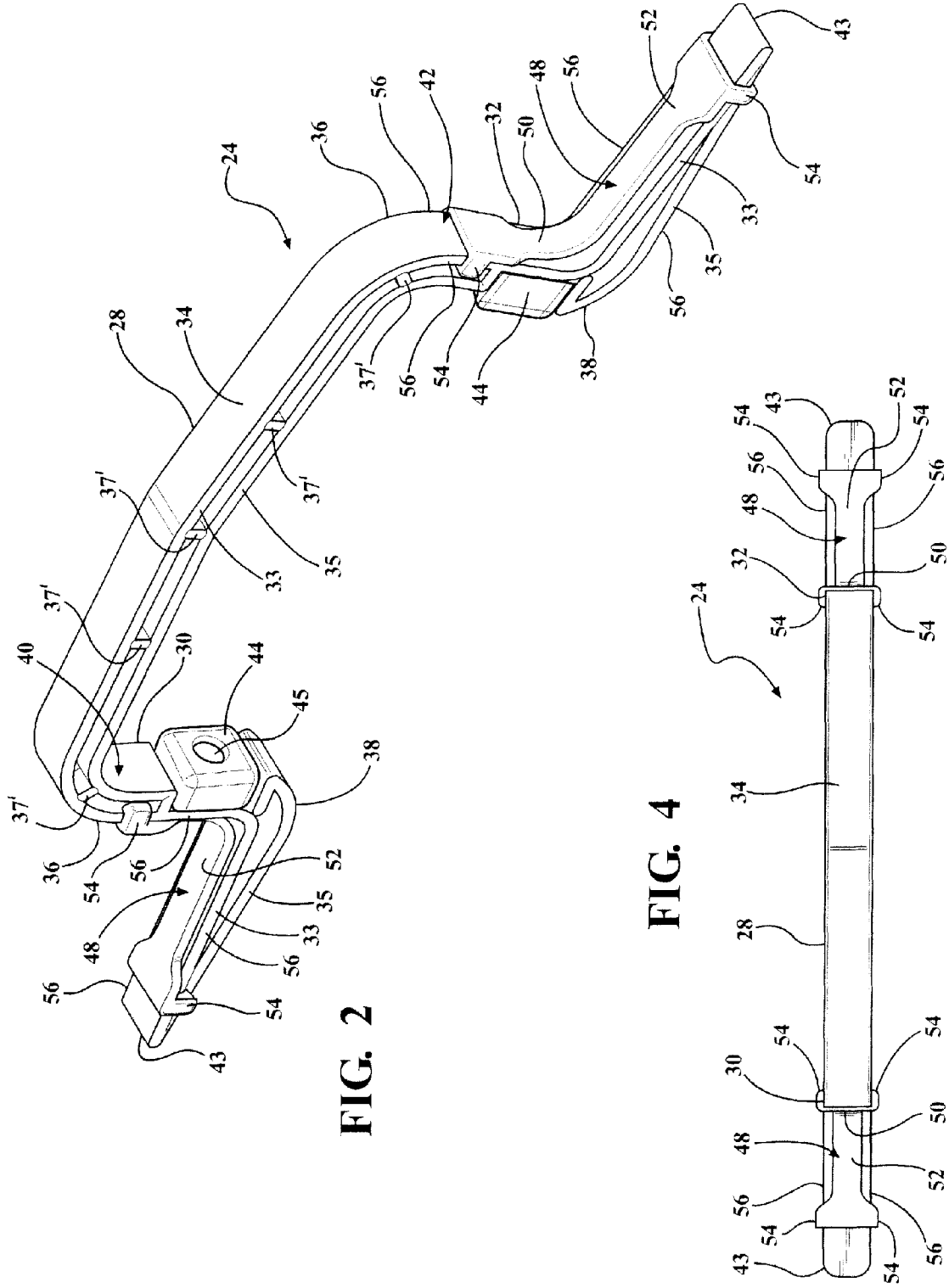

FLUOROSCOPY C-ARM DRAPE CLIP, DRAPE CLIP ASSEMBLY AND METHOD OF CLIPPING A STERILE DRAPE TO A FLUOROSCOPY C-ARM

CROSS-REFERENCE TO RELATED APPLICATIONS

This application claims the benefit of U.S. Provisional Application Ser. No. 61/513,074, filed Jul. 29, 2011, which is incorporated herein by reference in its entirety.

BACKGROUND OF THE INVENTION

1. Technical Field

This invention relates generally to sterile drapes for fluoroscopy equipment, and more particularly to fastening mechanisms configured to attach sterile drapes to a fluoroscopy C-arm.

2. Related Art

It is common to apply sterilized drapes to medical equipment used in medical procedures to prevent having to sterilize the equipment itself. The drapes present an external sterile surface to facilitate the avoidance of contaminating a patient. Though desirable to apply sterilized drapes to various types of medical equipment, it can prove challenging and costly to apply the drapes to the equipment due to the configurations of the medical equipment and the drapes themselves.

One such type of medical equipment typically requiring sterile drapes to be applied thereto is known as a fluoroscopy C-arm imaging unit. In particular, the fluoroscopy C-arm imaging unit typically requires a bag-shaped drape about an upper imaging head, a bag-shaped drape about a lower imaging head and a drape about an inner surface of a C-shaped arm, referred to as "C-arm", of the unit.

The C-arm is commonly provided having a generally rectangular shape, as viewed in lateral cross-section, with opposite flat inner and outer surfaces (though extending in arced fashion) extending between opposite flat sides. During an imaging procedure, the arced inner surface in exposed toward the patient, and thus, it is most important that the inner surface be covered by the sterile C-arm drape. To facilitate attaching a sterile drape to cover the inner surface, the opposite sides of the C-arm are provided with a groove extending along the length of the C-arm. The groove is configured for receipt of tabs on opposite arms of a clip to which the C-arm drape is fixed. Accordingly, the tabs on the clip must be oriented properly on the arms and sized properly for receipt in the respective grooves. Further, the arms of the clip must be laterally spaced from one another a predetermined distance to extend immediately adjacent the opposite sides of the C-arm for the tabs to be received in the grooves. However, C-arms come in a variety of widths, the distance extending between the opposite sides, and thus, the clips are produced having different widths, the distance extending between the opposite arms, for application specific use. Accordingly, one size clip is generally suitable for use with a specific width C-arm and not a different width C-arm. As such, a supply of the different size clips must be maintained, depending on the type and size of C-arms being used. Having to provide grooves in the sides of the C-arm adds cost to the manufacture process of the C-arm, and further, can provide a location for the buildup of contamination. In addition, having to stock and/or order a specific size drape clip, depending on the size of the C-arm, can increase inventory requirements and costs associated therewith. In addition, the proper size drape clip must be ordered and received, otherwise, if a mistake in ordering or delivery is made, the drape clip may not function with the C-arm.

A drape clip constructed in accordance with the invention at least overcomes those disadvantages of known drape clips discussed above, as well as others disadvantages, as will be apparent to one possessing ordinary skill in the art upon viewing the disclosure herein.

SUMMARY OF THE INVENTION

In accordance with one aspect of the invention, a fluoroscopy C-arm drape clip for attaching a sterile drape to a C-arm of a fluoroscopy C-arm imaging unit is provided. The drape clip includes a generally U-shaped band having a pair of legs and an arm. Each of the legs has a first end attached to the arm and a second end spaced from the arm. The legs extend away from the arm in substantially non-parallel, laterally spaced relation with one another when in a relaxed, unbiased state, and have inner surfaces facing one another and an outer surfaces facing away from one another. Further, an elastic pad is attached to the inner surface of each of the legs adjacent the second ends.

In accordance with another aspect of the invention, a C-arm drape and clip assembly configured for attachment to a C-arm of a fluoroscopy C-arm imaging unit is provided. The assembly includes a plurality of generally U-shaped bands each having a pair of legs and an arm. Each of the legs has a first end attached to the arm and a second end spaced from the arm. The legs extend away from the arm in non-parallel, laterally spaced relation with one another when in a relaxed, unbiased state, and have inner surfaces facing one another and an outer surfaces facing away from one another. An elastic pad is attached to the inner surface of each of the legs adjacent the second ends. Further, a sterile drape is operably attached to the outer surface of the legs.

In accordance with yet another aspect of the invention, a method of providing a sterile outer surface on a C-arm of a fluoroscopy C-arm imaging unit is provided. The method includes providing a C-arm imaging unit having a C-arm with a concave inner surface and a convex outer surface extending between opposite sides. Further, providing a plurality of generally U-shaped bands each having a pair of legs and an arm interconnecting the legs with an elastic pad attached to an inner surface of each of the legs such that the elastic pads face one another. Then, attaching an elongate sterile drape to the bands. Further yet, biasing the legs of the bands away from one another and disposing the arms about the opposite sides of the C-arm to bring the pads into frictional engagement with the opposite sides of the C-arm.

BRIEF DESCRIPTION OF THE DRAWINGS

These and other aspects, features and advantages of the present invention will become more readily appreciated when considered in connection with the following detailed description of presently preferred embodiments and best mode, appended claims and accompanying drawings, in which:

FIG. 2 is a perspective view of a drape clip constructed in accordance with another aspect of the invention;

FIG. 4 is a top view of the drape clip of FIG. 2.

DETAILED DESCRIPTION OF PRESENTLY PREFERRED EMBODIMENTS

Figure 1:
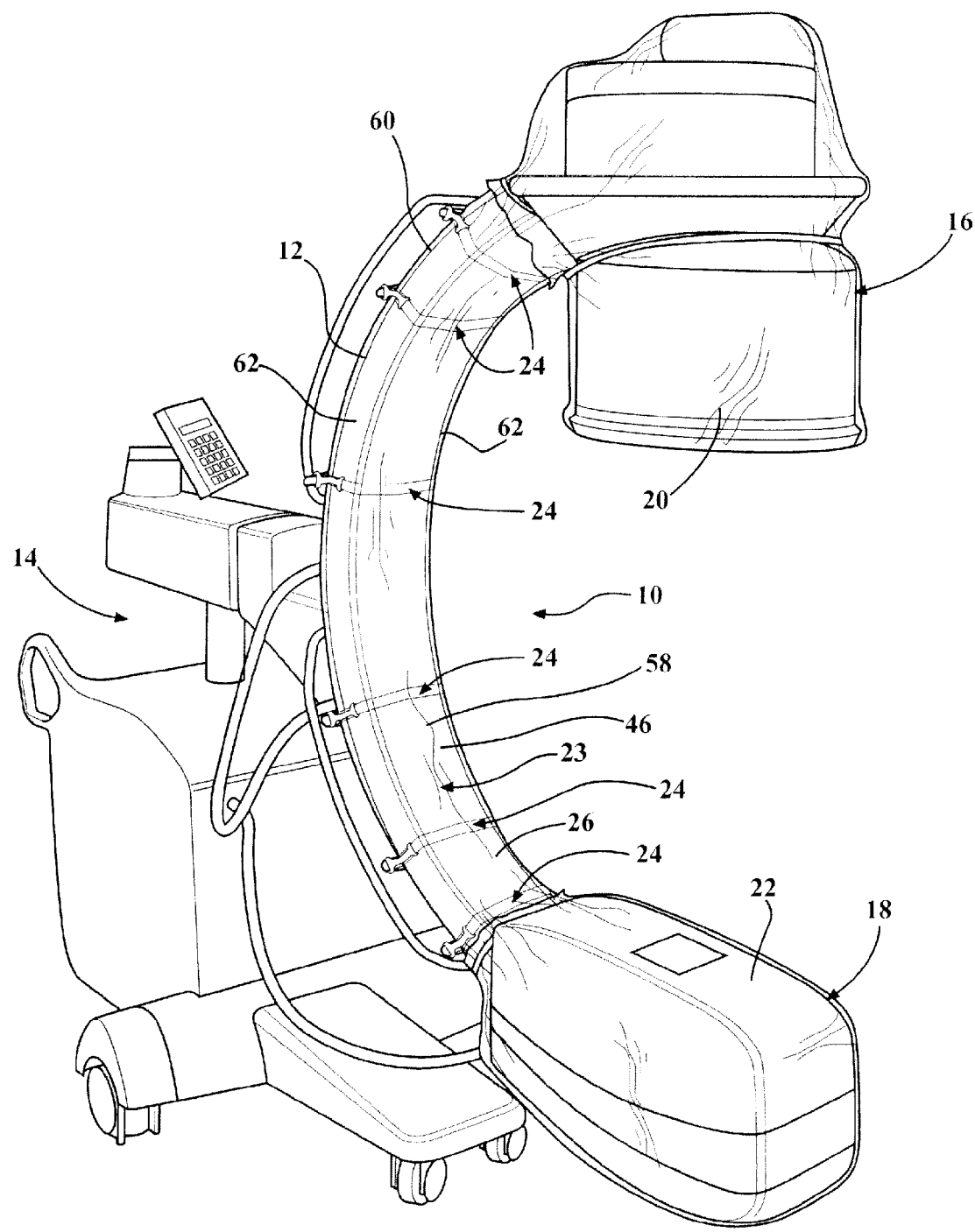
FIG. 1 is a perspective view of a fluoroscopy C-arm imaging unit with a pair of drapes disposed about upper and lower imaging heads and a sterile C-arm drape constructed in accordance with one aspect of the invention attached to a C-arm of the unit.

Referring in more detail to the drawings, FIG. 1 illustrates a C-arm drape and clip assembly, referred to hereafter as assembly 10, configured for attachment to a C-arm 12 of a fluoroscopy C-arm imaging unit 14. In addition to the assembly 10, a pair of drapes 16, 18 are shown disposed about upper and lower imaging heads 20, 22 of the imaging unit 14. In combination with one another, the assembly 10 and the drapes 16, 18 provide a sterile outer surface 23 about the C-arm imaging unit 14, thereby preventing the sterile area within a surgical theater, typically defined as the area extending above an upper surface of a surgical table, from becoming contaminated. The assembly 10 includes a plurality of bands, also referred to as clips 24, attached to a sterile drape 26, wherein the clips 24 are configured to releasably secure the drape 26 to the C-arm 12 in a reliable, simple manner, regardless of the size (i.e. width and depth) of the C-arm 12.

Figure 3A:
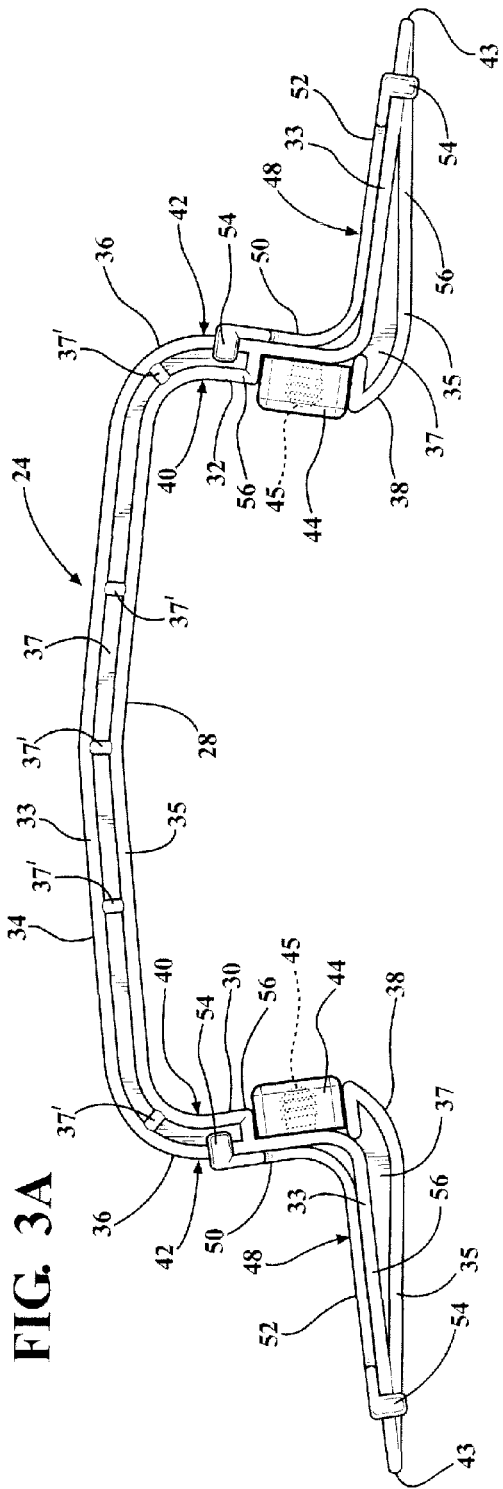
FIG. 3A is a front view of the drape clip of FIG. 2 shown in a relaxed, unbiased state.
Figure 3B:
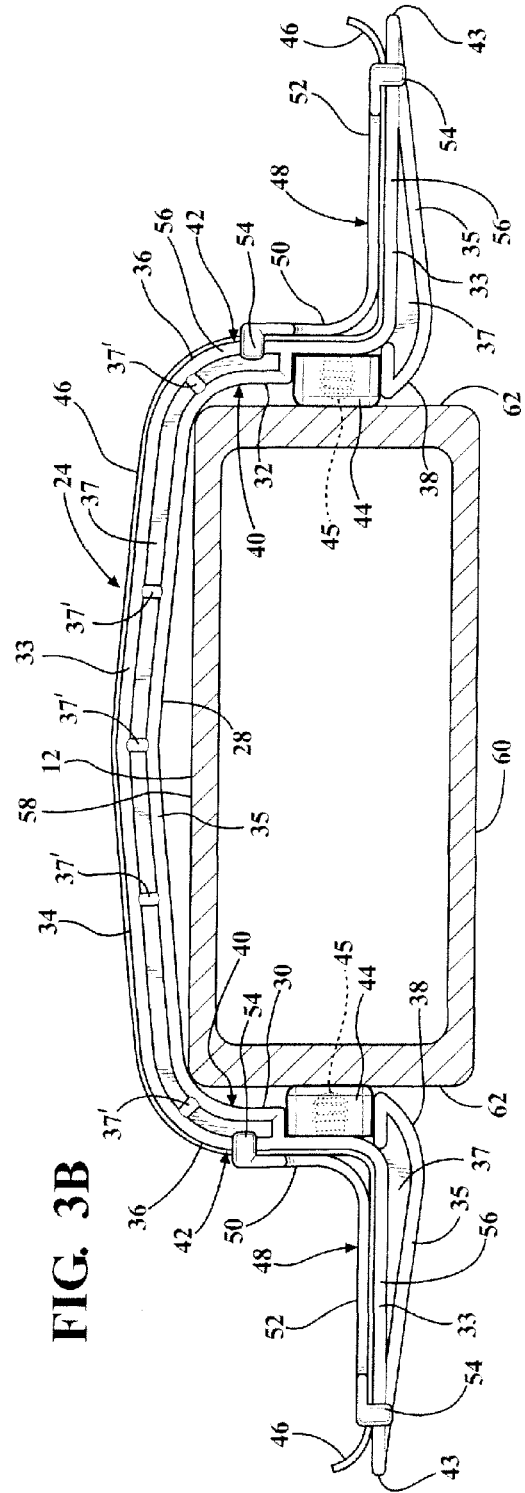
FIG. 3B is a front, partial cross-sectional view of the drape and clip assembly of FIG. 2 shown fastened to the C-arm of the C-arm imaging unit.

The clips 24 are formed from a moldable polymeric material, such as HDPE, and preferably as a monolithic piece of material. As best shown in FIGS. 2-4, the clips 24 each have a generally U-shaped band 28 having a pair of legs 30, 32 and an arm 34 extending between the legs 30, 32. Each of the legs 30, 32 have a first end 36 attached to the arm 34 and a second end 38 spaced from the arm 34. The legs 30, 32 extend away from the arm 34 in non-parallel, laterally spaced relation with one another when in a relaxed, unbiased state and have inner surfaces 40 facing one another and outer surfaces 42 facing away from one another. As best shown in FIG. 3A, the legs 30, 32 converge toward one another from the first ends 36 extending toward the second ends 38. As such, a spring bias is imposed by the legs 30, 32 when they are brought into parallel or substantially parallel relation with one another, such as slightly before becoming parallel or slightly beyond parallel upon attachment of the clips 24 to the C-arm 12 (FIG. 3B). Further, a pair of flanges, also referred to as extensions 43, are shown extending laterally outwardly from the second end 38 of each leg 30, 32, such that the legs 30, 32 and respective extensions 43 are generally L-shaped.

The arm 34 is molded having an upper wall 33 and a lower wall 35 spaced from one another by at least one rib, and shown as a plurality of ribs 37. One of the ribs 37 extends lengthwise along the arm 34, such as centrally between opposite edges from one end toward an opposite end and other of the ribs 37' extend widthwise along the arm from one edge toward the opposite edge. Further, each of the legs 30, 32 includes the upper wall 33 and the lower wall 35 spaced from one another by at least one rib, shown as the lengthwise rib 37. Accordingly, the clip 24 is generally H-shaped in lateral cross-section taken in spaced relation from the widthwise ribs 37'. The dual wall construction with intervening ribs provides the clip 24 with a lightweight construction, while at the same time, provides the clip 24 with a desired high strength and a degree of rigidity, while also being sufficiently resilient and elastic to provide the desired spring bias between the legs 30, 32 and arm 34 to maintain the assembly 10 in fixed retention on the C-arm 12 while in use.

Each leg 30, 32 has an elastic pad 44 attached to the inner surface 40 adjacent the second end 38. The elastic pads 44 are constructed of a material different from the that of the clip 24, such as from a thermoplastic elastomer or rubber, wherein the pads 44 provide a source of gripping static friction against the C-arm 12 in use in combination with the spring biased imposed by the legs 30, 32. Accordingly, the pads 44 restrain the clips 24 against relative movement with the C-arm 12. The pads 44 can be affixed to the clip 24 using any variety of fasteners, including adhesives, mechanical fasteners, and shown as being fixed on a press-type tree fastener 45 that can be integrally molded as a monolithic piece of material with the clip 24, or provided as a separate component, by way of example.

A sterile drape 46 (FIG. 1) is operably attached to the outer surfaces 42 of the legs 30, 32 and the extensions 43. In the embodiment illustrated, fasteners, also referred to as retainer members 48, are used to fasten the drape 46 against the outer surfaces 42 of the clips 24. The retainer members 48, by way of example and without limitation, are shown as being generally L-shaped, having a first portion 50 configured to overlie and fasten to the respective leg 30, 32, and a second portion 52 configured to overlie and fasten to the extension 43. The retainer members 48 are releasably attached to the clips 24, such as via C-shaped fingers 54 configured to clip around sides edges 56 of the legs 30, 32 and extensions 43. As such, the drape 46 can be selectively attached and removed from the clips 24 by attaching and removing the retainer members 48. Otherwise, it is contemplated that the sterile drape 26 can be permanently fixed to the outer surfaces 42 of the clips 24, such a by way of tack weld or adhesive, for example.

In accordance with another aspect of the invention, a method of providing a sterile outer surface 23 on a C-arm 12 of a fluoroscopy C-arm imaging unit 14 is provided. The method includes providing the C-arm imaging unit 14 with the C-arm 12 having a concave inner surface 58 and a convex outer surface 60 extending between opposite sides 62, wherein the sides 62 can be provided a uninterrupted, flat surfaces, if desired. Further, providing a plurality of generally U-shaped bands 24 each having a pair of legs 30, 32 and an arm 34 interconnecting the legs 30, 32 with an elastic pad 44 attached to an inner surface 40 of each of the legs 30, 32 such that the elastic pads 44 face one another. Further yet, attaching an elongate sterile drape 26 to the bands 24; biasing the legs 30, 32 of the bands 24 away from one another and disposing the legs 30, 32 about the opposite sides 62 of the C-arm 12 to bring the pads 44 into biased frictional engagement with the opposite sides 62 of the C-arm 12. With the legs 30, 32 being readily biased away from one another to a parallel or beyond parallel relation with one another, the bands 24 and drape 26 can be easily and quickly attached to a C-arm of varying widths and depths without concern of having to have a specific configuration for the particular C-arm 12. Accordingly, the drape and clip assembly 10 is useful for many differing C-arm configurations, thereby eliminating the need to have inventory of varying sizes of clips. Of course, it should be recognized that C-arm clips 24 constructed in accordance with the invention can be sized for targeted use with a particular size C-arm 12, if desired. Accordingly, one clip 24 may be sized differently from another clip 24, if intended for a specific size C-arm 12.

Many modifications and variations of the present invention are possible in light of the above teachings. It is, therefore, to be understood that the invention may be practiced otherwise than as specifically described, and that the scope of the invention is defined by any ultimately allowed claims.

What is claimed is:

1. A fluoroscopy C-arm drape clip for attaching a sterile drape to a C-arm of a fluoroscopy C-arm imaging unit, comprising:

a generally U-shaped band having a pair of legs and an arm extending between said legs, each of said legs having a first end attached to said arm and a second end spaced from said arm, said legs extending away from said arm in non-parallel, laterally spaced relation with one another when in a relaxed, unbiased state, and having inner surfaces facing one another and outer surfaces facing away from one another, further including flanges extending from said second ends away from one another such that said legs and their respective flanges are generally L-shaped, said legs, said arm, and said flanges being constructed as a monolithic piece of material;

an elastic pad attached to said inner surface of each of said legs adjacent said second ends; and further including generally L-shaped fasteners constructed from material separate from said monolithic piece of material, said fasteners being configured for operable attachment to said legs and said flanges.

2. The fluoroscopy C-arm drape clip of claim 1 wherein said legs converge toward one another from said first end toward said second end.

3. The fluoroscopy C-arm drape clip of claim 1 wherein said band is constructed of a first material and said elastic pads are constructed of a second material, said first material being different from said second material.

4. The fluoroscopy C-arm drape clip of claim 1 wherein said arm has an upper wall and a lower wall spaced from one another by at least one rib.

5. The fluoroscopy C-arm drape clip of claim 4 wherein said upper wall and said lower wall are spaced from one another by a plurality of said at least one rib.

6. The fluoroscopy C-arm drape clip of claim 5 wherein one of said ribs extends lengthwise along said arm and other of said ribs extends widthwise along said arm.

7. The fluoroscopy C-arm drape clip of claim 4 wherein each of said legs has an upper wall and a lower wall spaced from one another by at least one rib.

8. The fluoroscopy C-arm drape clip of claim 1 wherein said arm is generally H-shaped in lateral cross-section.

9. The fluoroscopy C-arm drape clip of claim 1 wherein said pads are a thermoplastic elastomer.

10. The fluoroscopy C-arm drape clip of claim 9 wherein said band is HDPE.

11. The fluoroscopy C-arm drape clip of claim 1 wherein said arm has a central apex.

12. A C-arm drape and clip assembly configured for attachment to a C-arm of a fluoroscopy C-arm imaging unit, comprising:

a plurality of generally U-shaped bands each having a pair of legs and an arm, each of said legs having a first end attached to said arm and a second end spaced from said arm, said legs extending away from said arm in non-parallel, laterally spaced relation with one another when in a relaxed, unbiased state, and having inner surfaces facing one another and outer surfaces facing away from one another, further including flanges extending from said second ends away from one another such that said legs and their respective flanges are generally L-shaped, said legs, said arm, and said flanges being constructed as a monolithic piece of material;

an elastic pad attached to said inner surface of each of said legs adjacent said second ends;

a sterile drape; and a plurality of generally L-shaped fasteners constructed from material separate from said monolithic piece of material, said fasteners having generally C-shaped fingers configured for operable attachment to said legs and said flanges to capture said sterile drape between said legs, said flanges and said fasteners.

13. The assembly of claim 12 wherein said legs converge toward one another from said first end toward said second end.

14. The assembly of claim 12 wherein said band is constructed of a first material and said elastic pads are constructed of a second material, said first material being different from said second material.

15. The assembly of claim 12 wherein said arm has an upper wall and a lower wall spaced from one another by at least one rib.

16. The assembly of claim 15 wherein said upper wall and said lower wall are spaced from one another by a plurality of said at least one rib.

17. The assembly of claim 16 wherein one of said ribs extends lengthwise along said arm and other of said ribs extends widthwise along said arm.

18. The assembly of claim 15 wherein each of said legs has an upper wall and a lower wall spaced from one another by at least one rib.

* * * * *